United States Patent [19]
van der Veen et al.

[11] Patent Number: 5,454,836
[45] Date of Patent: Oct. 3, 1995

[54] VDD (R) PACING SYSTEM

[75] Inventors: Johannes S. van der Veen, Arnhem; Gustaaf A. Stoop; Frits M. van Krieken, both of Dieren, all of Netherlands

[73] Assignee: Vitatron Medical, B.V., Dieren, Netherlands

[21] Appl. No.: 184,218

[22] Filed: Jan. 18, 1994

[51] Int. Cl.$^6$ ................................................ A61N 1/362
[52] U.S. Cl. ................................................................ 607/9
[58] Field of Search ............................................ 607/9, 27

[56] References Cited

U.S. PATENT DOCUMENTS 4,513,743   4/1985   van Arragon et al. .
5,065,759  11/1991   Begemann et al. .
5,247,930   9/1993   Begemann et al. ........................ 607/11

*Primary Examiner*—William E. Kamm
*Assistant Examiner*—Scott M. Getzow
*Attorney, Agent, or Firm*—Woodcock, Washburn, Kurtz, Mackiewicz & Norris

[57]  ABSTRACT

A VDD-type pacing system which may have a floating atrial electrode analyzes P-wave events and absences of P-waves to determine data indicative of the likelihood of P-wave undersensing. The pacemaker logic chooses a reaction algorithm to respond to atrial events in accordance with whether an absence of a P-wave is more likely to have been an undersense or an incidence of bradycardia. Specific algorithms are presented which illustrate pacemaker reactions to probable undersense and brady occurrences. The pacemaker also incorporates a subsystem for detection of undersense events.

29 Claims, 14 Drawing Sheets

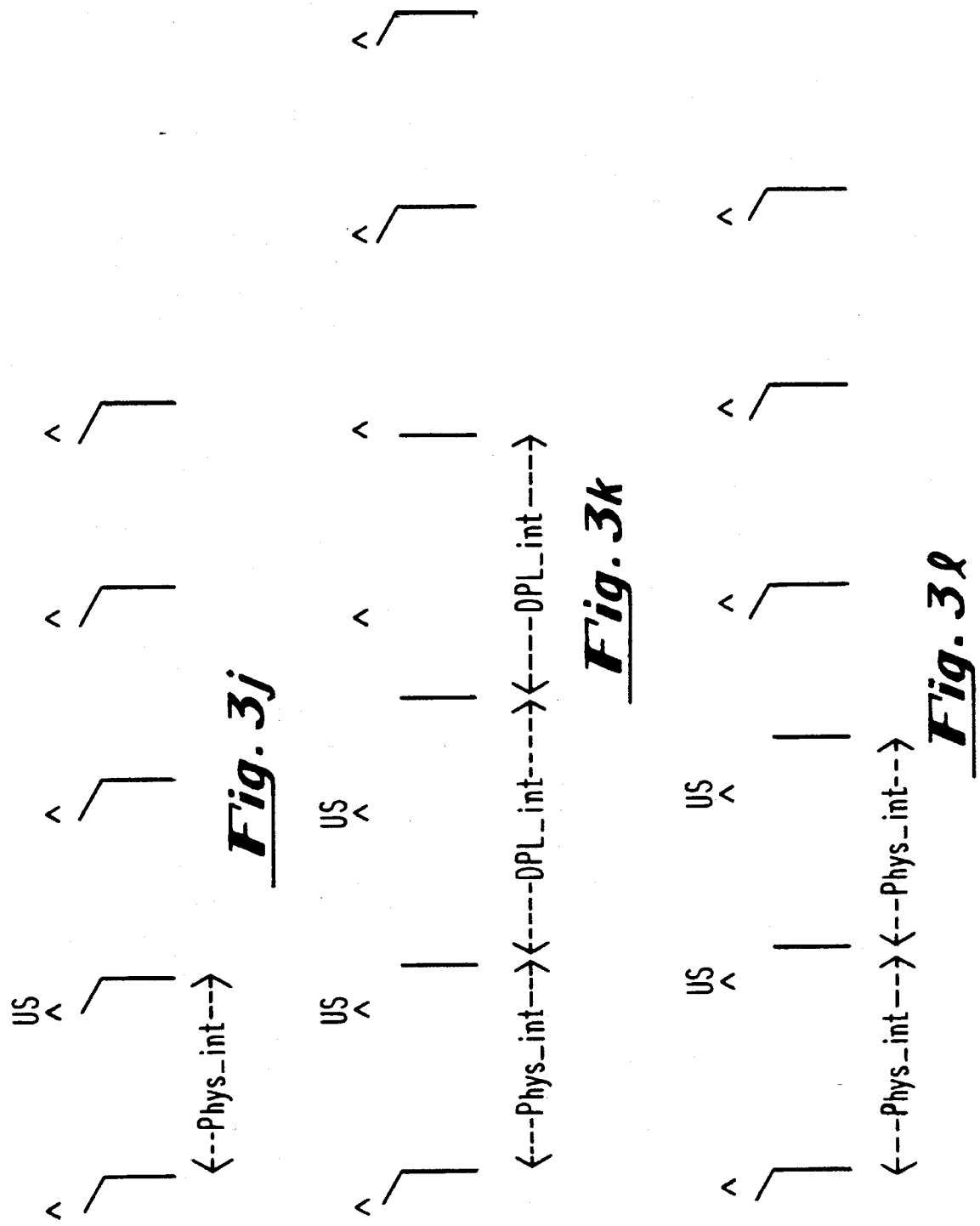

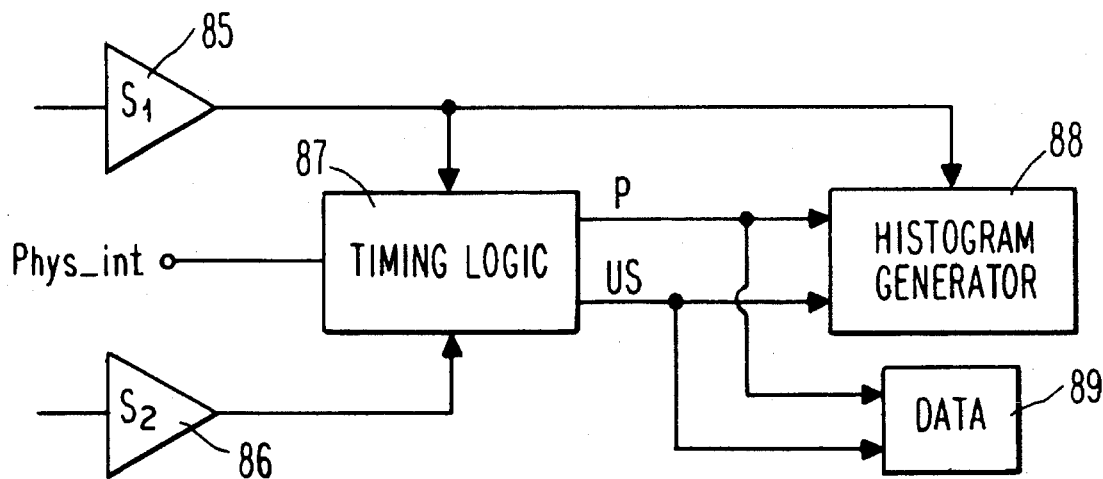
_Fig. 4a_
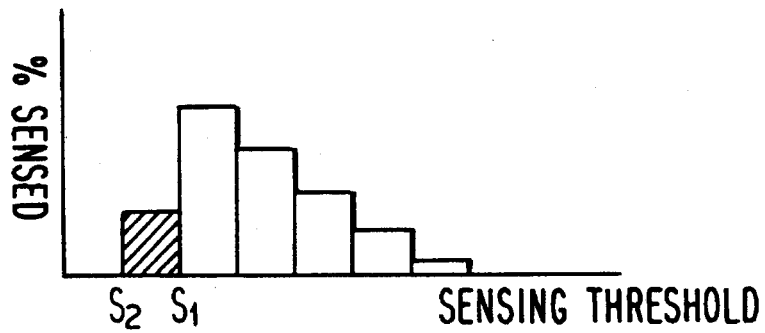
_Fig. 4b_
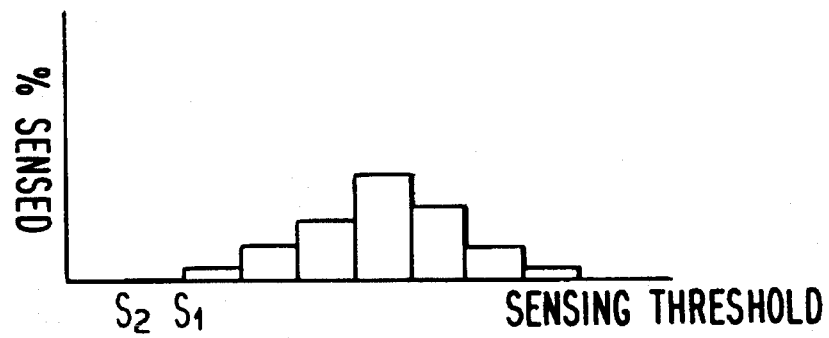
_Fig. 4c_

A-A int AVAILABLE

A-A int AVAILABLE

A-A int NOT AVAILABLE

VDD (R) PACING SYSTEM

FIELD OF THE INVENTION

This invention lies in the area of dual chamber cardiac pacemakers and the method of operation of same and, more particularly, VDD mode pacemaker systems.

DESCRIPTION OF THE PRIOR ART

Dual chamber rate responsive pacemakers are now widely available from pacemaker manufacturers. Such pacemakers may be of many types, including the types designated as DDDR or VDDR. The DDD pacemaker paces and senses in both chambers, i.e., both the atrium and the ventricle, and the DDDR pacemaker additionally has rate responsive (RR) backup to provide pacing in the absence of sensed natural beats, or to provide rate responsive ventricular pacing during atrial tachyarrhythmias in the absence of natural ventricular beats. The DDD or DDDR pacemaker has a lead that is placed within the atrium to deliver atrial pace pulses, as well as to sense natural atrial (sinus) signals, and a ventricular lead for pacing and sensing in the ventricle. In contrast, the VDD or VDDR pacemaker paces only in the ventricle, although it senses in both the atrium and the ventricle. The VDD or VDDR pacemaker system may be made simpler by incorporating a single lead which has a floating atrial electrode for sensing atrial signals, in a known manner. Hereinafter, DDD(R) is used to refer to either a DDD or DDDR pacemaker, and VDD(R) is used to refer to either a VDD or VDDR pacemaker. The VDD(R) pacemaker is indicated for patients who are determined to have a good and reliable sinus rate, so that for a good bit of the anticipated lifetime of the patient, natural atrial signals will be present from which ventricular pace pulses can be tracked, thereby providing synchronized pacing.

For DDD(R) and VDD(R) pacemakers, there is an inherent desirability of maximizing use of the sinus rate, i.e., tracking sensed atrial signals as long as a good atrial signal is present and sensed. The normal response to an atrial sense is to deliver a ventricular pace after an AV delay in the absence of an earlier ventricular sense, i.e., to track the atrial signal, in a synchronized manner. Any problem which interferes with the pacemaker's ability to track is, of course, a matter of concern. For VDD(R) systems, the possibility of failing to sense an atrial signal (P-wave) so as to enable tracking is such a problem. Such a failure is called an "undersense" (US), and the resultant loss of atrial tracking can lead to negative hemodynamic effects; ventricular rate irregularities; retrograde conduction; and other arrhythmogenic effects.

The floating atrial electrode of a VDD(R) pacemaker system has the recognized difficulty that low level P-wave signals occasionally may not be sensed. Since the electrode is floating in the atrial chamber, and not in direct contact with the atrial wall, the signal that is picked up is not as strong as is the case for an electrode positioned in contact with the heart wall. Thus, it is a recognized fact that such a VDD(R) system is vulnerable to occasional undersenses. In practice, the reaction of a pacemaker to an undersense is to assume bradycardia ("brady"), in which case a number of the following P-waves may also be lost, due to their timing. For example, following an undersense, the next atrial sense (AS) may be too early after the ventricular pace to be tracked, or it may be blanked during post-ventricular blanking. As a result, following a single US, it may be a number of cycles until the pacemaker is able to resume synchronous tracking. For example, and depending on atrial rate and certain pacemaker settings, an undersense rate of 2% may lead to significantly more than 2% loss of tracking. The problem is thus a serious one, and one which heretofore has not been satisfactorily resolved.

A difficulty that a designer faces in attempting to solve the undersensing problem in a VDD(R) system is that many instances of no atrial sense really represent a brady situation, i.e., the atrial rate has slowed such that no P-wave is sensed before time out of the ventricular escape interval. In these cases, the pacemaker should be designed to react in accordance with a true brady situation. This means that the problem cannot be solved by reacting to every instance of no atrial sense by assuming an undersense and taking corrective measures for a US. On the other hand, the conventional reaction, which assumes brady, fails to meet the problems caused when in fact there has been an undersense. The conventional brady-type reaction comprises a V-pace delivered either at LRL, DPL or optionally at either of the above with a hysteresis-extension for the first beat. The disadvantages of this conventional reaction are that hysteresis may remain disabled for a long period (until the A-rate exceeds the pacing rate), which is a problem where the A-rate is in the hysteresis range, and also, for the conventional reaction, there may be large V-rate jumps when occasional atrial senses are tracked during an episode of atrial bradycardia; resynchronization after a single US can take a long time.

In the pacemaker system of this invention, the undersense problem in the VDD(R) system is met by providing the pacemaker with information as to when the undersense situation is likely. It is a basic assumption that US or brady occurs for sufficiently long periods that the pacer can detect and learn that one or the other is occurring. If it is determined that an undersense situation is relatively likely, the pacemaker utilizes an algorithm designed to react optimally to the occurrence of a US. However, if the undersense situation is not deemed likely, then the pacemaker reacts by assuming that the lack of an atrial sense is a normal brady situation. By thus determining that the absence of an atrial sense is more likely US, or more likely brady, the pacemaker reacts accordingly and optimizes pacemaker response. After some learning, this results in a reduction of atrial signals which are not properly tracked. Specifically, the invention disclosed herein provides for faster resynchronization after an undersense occurrence, and faster resynchronization in the situation where the atrial rate is in a hysteresis area and there is an initial loss of hysteresis due to the undersense.

SUMMARY OF THE INVENTION

In view of the above object of providing a VDD(R)-type pacemaker system which more optimally reacts to either undersense or brady situations, there is provided a pacemaker system having software and/or hardware for actively collecting historic information from which to determine the relative likelihood of brady and US occurrences, and to anticipate and detect US occurrences. The pacemaker cyclically analyzes such information and when a cycle concludes with no atrial sense, the pacemaker determines whether the absence of an atrial sense is more likely characterized by an undersense or by a brady condition. Following this determination, the pacemaker selects an appropriate algorithm and prepares an appropriate reaction, assuming either a US or brady condition. If the accumulated information does not indicate a likelihood one way or the other, or if such information is determined to be unreliable or otherwise not available, the pacemaker system proceeds with a standard algorithm for reacting to a cycle with no atrial sense.

Two exemplary algorithms for responding to an undersense are provided for the pacemaker of this invention. In a first algorithm, if the pacemaker switches from tracking to pacing at the pacing limit, the pacemaker effectively reactivates hysteresis if there is an indication that there likely has been an undersense, in order to detect whether there is an underlying sinus signal within the hysteresis band of rates. If such an underlying sinus is found, the pacemaker quickly returns to a tracking mode. In another algorithm based on the assumption that a condition of no atrial sense is an undersense, the escape interval is set equal to 1.5 times the running atrial average interval, i.e., the pacing rate is set to ⅔ of the atrial rate. This arrangement returns the pacemaker to tracking after just two slow pace pulses following an actual US.

The pacemaker determines the likelihood of US or brady by one or more of several means. For example, the pacemaker accumulates a P-wave histogram of automatically measured P-wave amplitude levels, which histogram is monitored to determine the likelihood of undersenses. Historic undersense information is obtained by accumulating events where the A-A interval of successive atrial senses is longer than the hysteresis limit interval, but approximately two times the running atrial average interval. Further, after a reaction has been chosen and employed, the pacemaker verifies whether or not the choice was correct, and updates the historic information accordingly.

BRIEF DESCRIPTION OF THE DRAWINGS

FIGS. 3f and 3g are timing diagrams illustrating the response of the algorithms shown in FIGS. 3d and 3e to an undersense; FIG. 3j, 3k and 3l are timing diagrams illustrating the response of the algorithms shown in FIGS. 3h and 3i to undersense events.

FIG. 4a is a simplified block diagram showing the primary components of a subsystem for determining P-wave data and data indicative of undersensing; FIG. 4b and 4c comprise P-wave amplitude histograms illustrating how accumulated data can indicate the relative probability of undersense conditions.

FIG. 5a is a logic flow diagram of another algorithm embodiment for the pacemaker of this invention for reacting to a probable undersense situation, and which employs an atrial hysteresis technique to regain tracking of an underlying sinus at a rate above the hysteresis limit. FIG. 5b illustrates criteria employed for determining when an A—A interval is available, as part of the determination made in FIG. 5a.

FIG. 6b is a rate diagram that corresponds to FIG. 6a; FIG. 6c is a modification of FIG. 5a which illustrates the logic path for each cycle of FIG. 6a.

FIG. 7b is a modification of FIG. 5a which illustrates the logic path for each cycle of FIG. 7a.

DESCRIPTION OF THE PREFERRED EMBODIMENTS

As used in this application, the terms "sinus rate" and "atrial rate" are used synonymously, i.e., they both refer to the rate of a natural atrial beat. The term "pacing limit" refers to the rate at which the pacemaker is currently set to deliver pace pulses. It is recognized that the pacemaker may be a rate responsive pacemaker, and that additionally the pacing limit may be a dynamic pacing limit (DPL) which follows a sensed atrial rate. Reference is made to U.S. Pat. No. 5,247,930, which is incorporated herein by reference. The term "hysteresis limit" is the rate that defines the lower edge of a hysteresis rate band below the pacing limit, hysteresis being used in the conventional manner of representing an extended escape interval. It is noted that when hysteresis is being used, the effective pacing limit is the hysteresis limit.

Figure 1A:
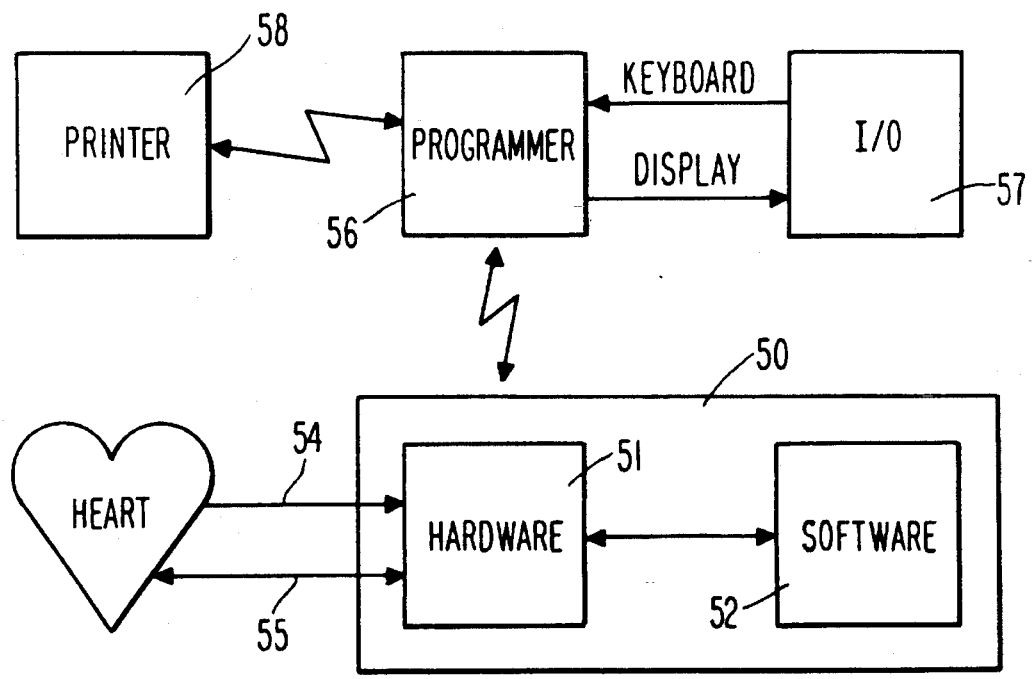
FIGS. 1a and 1b show block diagrams of the basic components of a VDD(R) pacemaker system as used in this invention.

The pacing system of this invention is preferably software-based, i.e., the software controls all functions through the hardware. Referring specifically to FIG. 1a, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and there may be one or more sensor connections 54. As is well understood in the art, for a DDD-type dual chamber pacemaker, there are generally two leads, an atrial lead and a ventricular lead, each lead having at least one electrode, unipole or bipole, positioned in the heart. For a VDD(R)-type pacemaker, there may be just one lead. The line 54 is illustrated as leading to the heart, as in a QT-type sensor arrangement, but may be attached to the outside case of the pacemaker or may couple to any other available sensor for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1a, the pacer 50 may be in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 1B:
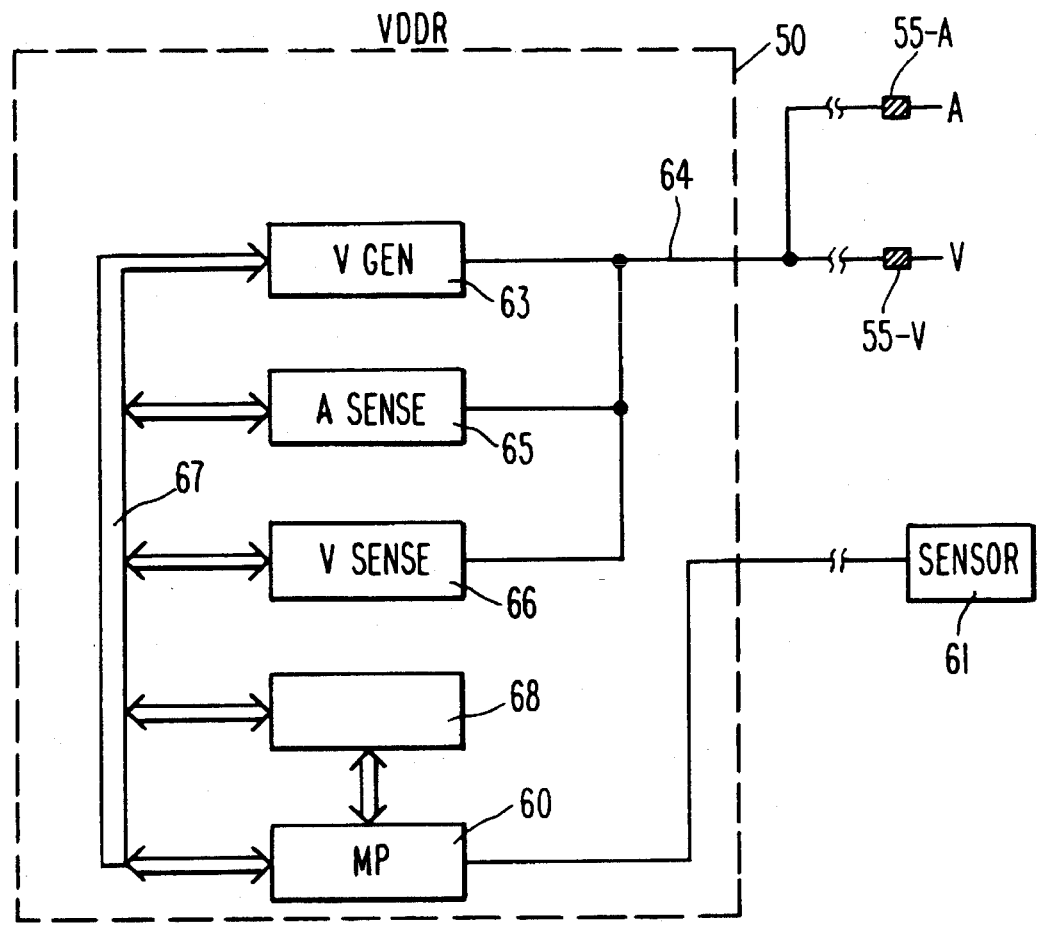

Referring to FIG. 1b, there is shown a basic block diagram of the primary hardware components of a VDD(R) pacer 50. A ventricular generator is illustrated which is connected to the patient's ventricle through lead 64. V sense amplifier 66 is also connected to lead 64, to receive and send signals from the patient's ventricle, provided by electrode 55-V. An A sense amplifier 65 is illustrated also connected to lead 64. Lead 64 may in fact comprise two separate leads, but is preferably a single lead with at least one floating atrial bipole 55-A for sensing atrial signals.

In one embodiment of this invention which preferably incorporates QT rate control, V sense block 66 also includes means for picking out and determining the timing of the evoked T wave. Generator 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. The microprocessor system suitably consists of a D43 microprocessor with 4k byte ROM and 624 bytes RAM (MC146805E2 compatible); and an M05 memory chip with 4k byte ROM and 256 bytes RAM. It is preferred that the operating software fit in 8k byte ROM, and have available for use 624 bytes of RAM; 256 bytes of RAM are held unused to enable future RAM routines (executable code located in RAM). In a manner well known in the art, the software contains a number of strategic places where escape points to a RAM routine are available. ks affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of the software enable one of ordinary skill in this art area to design a system for carrying out the functions within the scope of the invention. Data inputted from programmer 56 is stored in memory associated with the microprocessor.

Still referring to FIG. 1b, there is shown a sensor 61, indicated as providing an input to microprocessor system 60. Sensor 61 represents one or more sensors for monitoring one or more body parameters known to be indicative of desired pacing rate. Sensor 61 is illustrated as being outside the pacemaker, but may be physically located inside the pacemaker casing, as with certain activity sensors. Alternately, as is the case with the Q-T-type rate responsive pacemaker, the "sensor" information may be actually obtained from the ventricular lead, by extracting timing information relating to the Q-T interval. As used in the practice of this invention, the term sensor or sensor signal may refer to information obtained from any available rate responsive sensor-type source. Also, as used in the claims hereto, the term "rate signal" may refer to a signal deriving its information from either or both a sensor source and the sensed atrial rate.

In the detailed description of the pacing system of this invention, as well as the illustrative figures, the following acronyms and abbreviations are utilized:

| Symbol | Definition |
|---|---|
| $AA_{avg}$ | Running average of the natural sinus rate. This can be any measure of the recent atrial rate, and can be the phys__rate as defined in U.S. Pat. No. 5,247,930 |
| A-Hyst | Interval increment (in ms) added by atrial hysteresis |
| AA__int | interval between two atrial senses; also referred to as to A-A interval. AA rate corresponds to AA__int |
| AS | Atrial sense |
| BAS | Brady Atrial Sense |
| DPL | Dynamic Pacing Limit (flywheel rate); DPL__int is the interval corresponding to DPL |
| LPL | Lower Pacing Limit; LPL__int is the interval corresponding to LPL |
| NAS | Normal Atrial Sense |
| NOA | No atrial sense |
| UTL | Upper Tracking Limit |
| US | Undersense of P-wave |
| VP | Ventricular pace |
| V__esc | Ventricular escape interval |
| VS | Ventricular sense |

Figure 2:
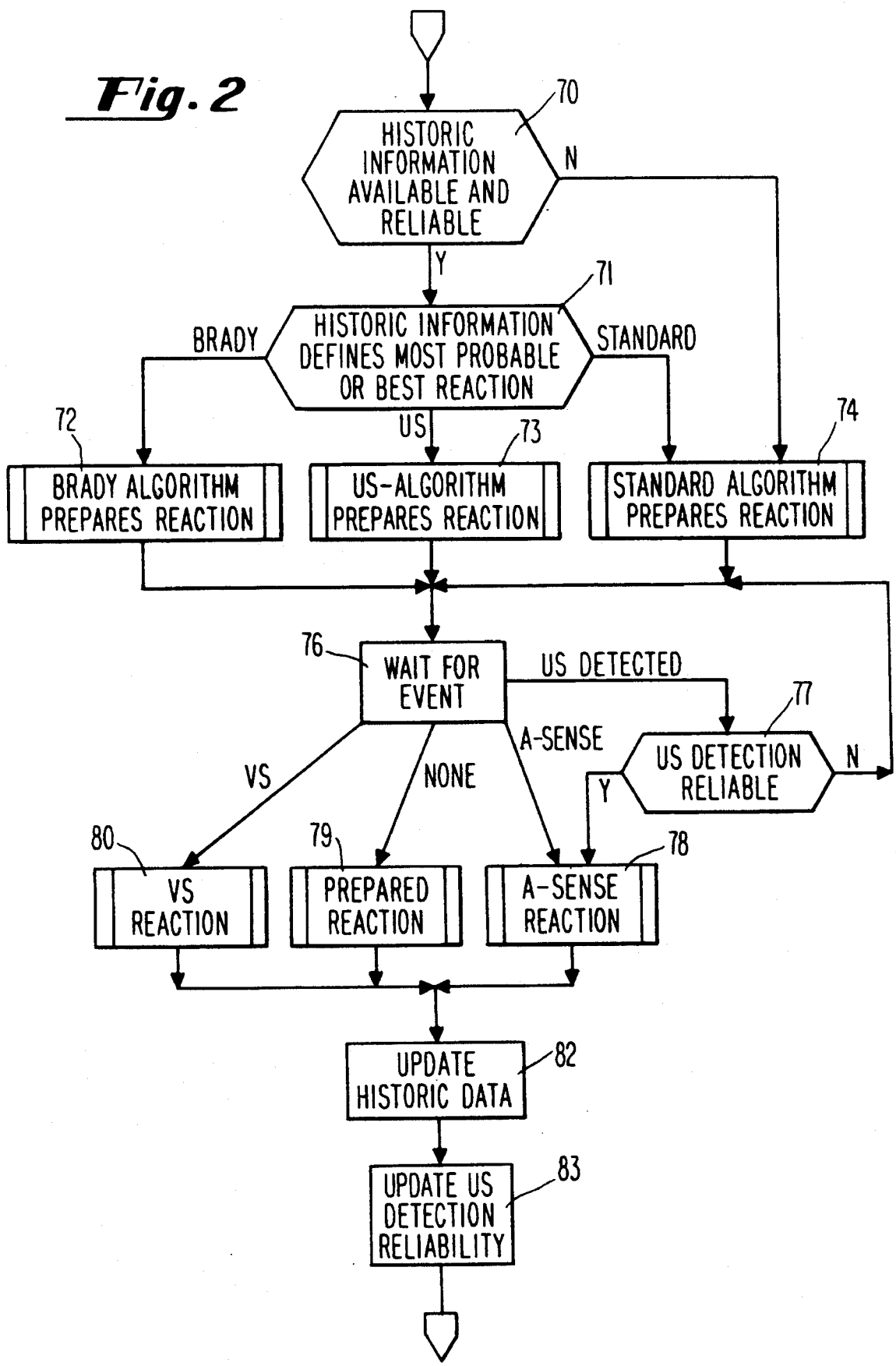
FIG. 2 is a logic diagram illustrating the primary logic steps taken in determining the reaction of the pacemaker system to different events, and particularly illustrating the use of accumulated historic information for choosing how to react to a situation which may be either an undersense or brady.

Referring now to FIG. 2, there is shown a flow diagram of the primary logic steps taken in the pacemaker system of this invention, which illustrates how the VDD(R) pacemaker reacts to the absence of an atrial sense, i.e., an NOA. As discussed above, the pacemaker logic can be premised upon the likelihood that this represents a bradycardia situation, or it can be premised on the likelihood that there has been an undersense. In the algorithm of FIG. 2, the pacemaker utilizes historic information that has been accumulated to determine the relative probabilities of these events, and in order to choose the best reaction. While specific examples of "historic" information are presented below, it is to be understood that the term generally embraces data accumulated on a cycle-by-cycle basis concerning patient and pacemaker events, and pacemaker operating data.

At block 70, the pacemaker algorithm determines whether historic information relative to undersense and brady is available and reliable. This information may be obtained in one or more different ways, as is illustrated more specifically in FIGS. 4a–4e, and discussed below. Historic information is judged available if enough relevant events have been accumulated at block 82 (discussed below). Thus, if the amount of data concerning brady episodes, US episodes, P-wave magnitudes, etc. is insufficient, then historic information upon which a decision can be made is deemed not to be available. Likewise, the reliability of the historic information is judged based upon the data accumulated at block 83 (discussed below), by determining if in enough cases the prepared US or brady reaction indeed corresponded with a real occurrence of US or brady. If such historic information is not both available and reliable, the routine branches to block 74 and prepares a standard logic algorithm for reacting to the next cycle. In this case, the standard algorithm can be a "default"-type algorithm, and may be one that assumes either brady or undersense. Thus, the standard algorithm may be programmed by the physician based upon his or her determination of the patient's situation.

Returning to block 70, if such historic information is available and reliable, the routine goes to block 71, where the information is processed to define the most probable or best reaction. The most probable, or best reaction, is likewise based on information accumulated at block 82. A first method of choosing the reaction is to simply prepare the reaction for the most likely event, i.e., is brady or US most likely in any situation where there is an absence of a sensed atrial signal? A second approach is to make a weighted choice, i.e., select a US reaction generally, but a brady reaction only if brady is much more likely. Alternately, the choice may be weighted toward brady, with a US reaction selected only if US is much more likely. If brady is selected, the routine branches to block 72, and selects a brady algorithm for reacting. If us is selected, the routine goes to block 73 and selects an undersense algorithm, wherein the pacemaker is prepared to react to the absence of a sensed signal on the basis that it is likely an undersense. If, at block 71, the information is ambiguous or not clear enough to define undersense probability, the routine branches to block 74, and selects a standard algorithm for preparing to react, e.g., a user-selected algorithm, or a default factory setting.

In order to illustrate the types of algorithms useful at blocks 72, 73 and 74, reference is now made to FIGS. 3a–3m. These algorithms provide respective different reactions to the absence of an atrial signal during a pacemaker cycle; each provides a different manner of reacting, or timing the reaction of the pacemaker. These algorithms are preferably software-embodied, but can be hardware-embodied within the scope of this invention. While other algorithms, or control logic sequences, may be used, these algorithms are exemplary for the pacemaker of this invention.

Figure 3A:
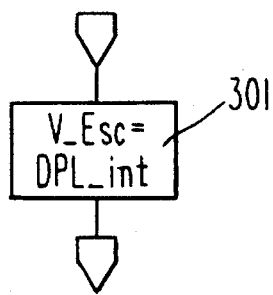
FIG. 3a is a simple flow diagram of a first and simplest method of reacting to brady.
Figure 3B:
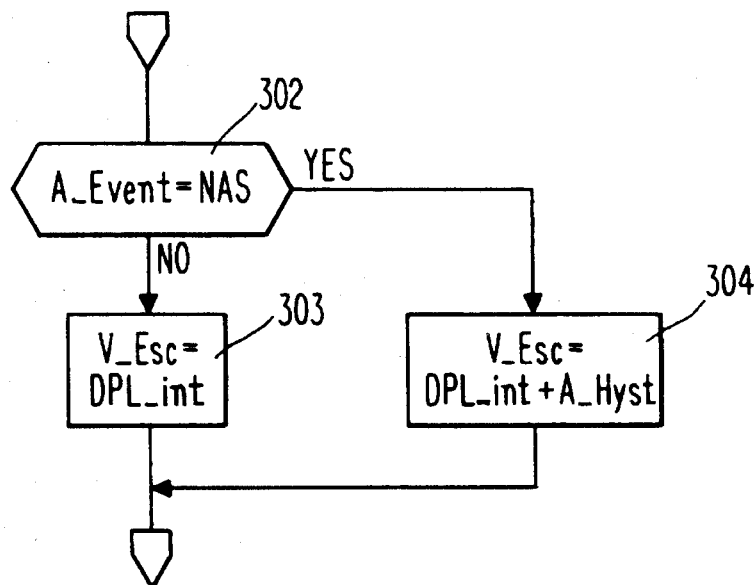
FIG. 3b is a simple flow diagram of a second brady reaction method.
Figure 3C:
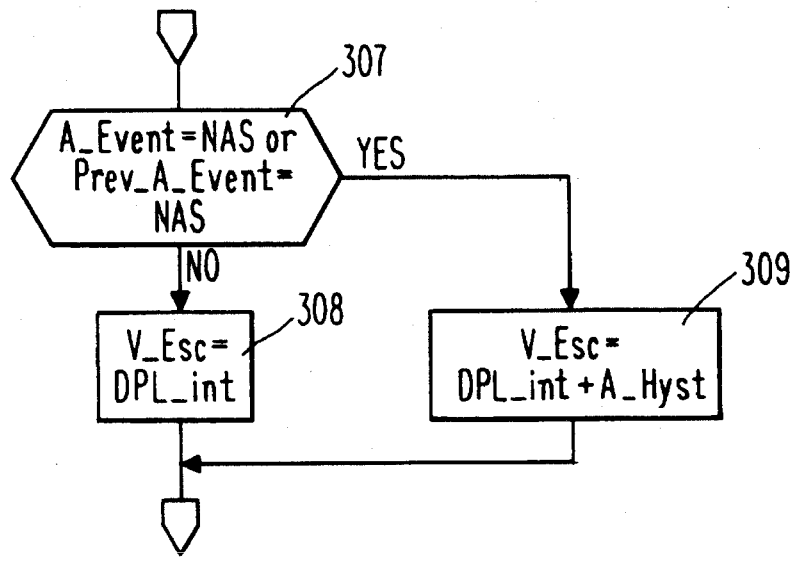
FIG. 3c is a simple flow diagram of a third brady reaction method.

With respect to block 72 of FIG. 2, FIGS. 3a, 3b and 3c show respective brady algorithms for pacemaker reaction to a situation which could potentially be either brady or undersense, but where a brady reaction is selected. In FIG. 3a, the reaction is simply to set the ventricular escape interval equal to the interval corresponding to the dynamic pacing limit, as shown at block 301. Thus, if the pacemaker times out the interval corresponding to the pacing limit without any intervening atrial or ventricular sense, then a ventricular pace is delivered at the timeout of DPL_int. Referring to FIG. 3b, there is shown a second brady reaction, where atrial hysteresis is used as long as there is a normal atrial sense (NAS). If an A event is found as an NAS, at 302, the pacemaker at 304 makes V_esc=DPL_int+A_Hyst. However, if a cycle is completed without a normal atrial sense, then ventricular escape interval equals DPL_int. Thus, FIG. 3b modifies FIG. 3a simply by providing atrial hysteresis as long as there is a NAS. FIG. 3c shows a further modification where atrial hysteresis is employed a second time. At 307, it is determined whether there has been an NAS or, in the absence of an NAS, the previous atrial event was an NAS. If yes, A_Hyst is again added to V_esc, as shown at 309. If no, the ventricular escape interval is simply set to DPL_int, as shown at 308. Of course, the algorithm of FIG. 3c may be modified to add A_Hyst for N cycles, FIG. 3c being simply an example where N=2.

Figure 3D:
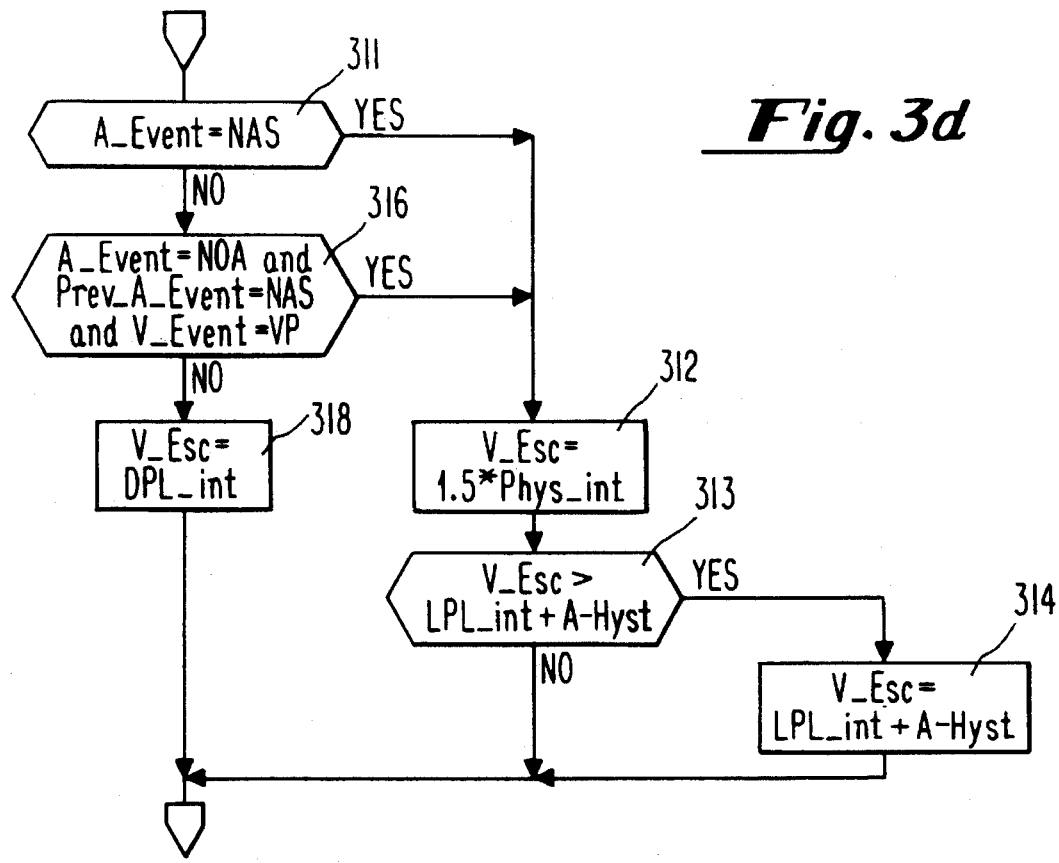
FIG. 3d is a simple flow diagram of a first undersense reaction algorithm for use with the pacemaker of this invention.
Figure 3E:
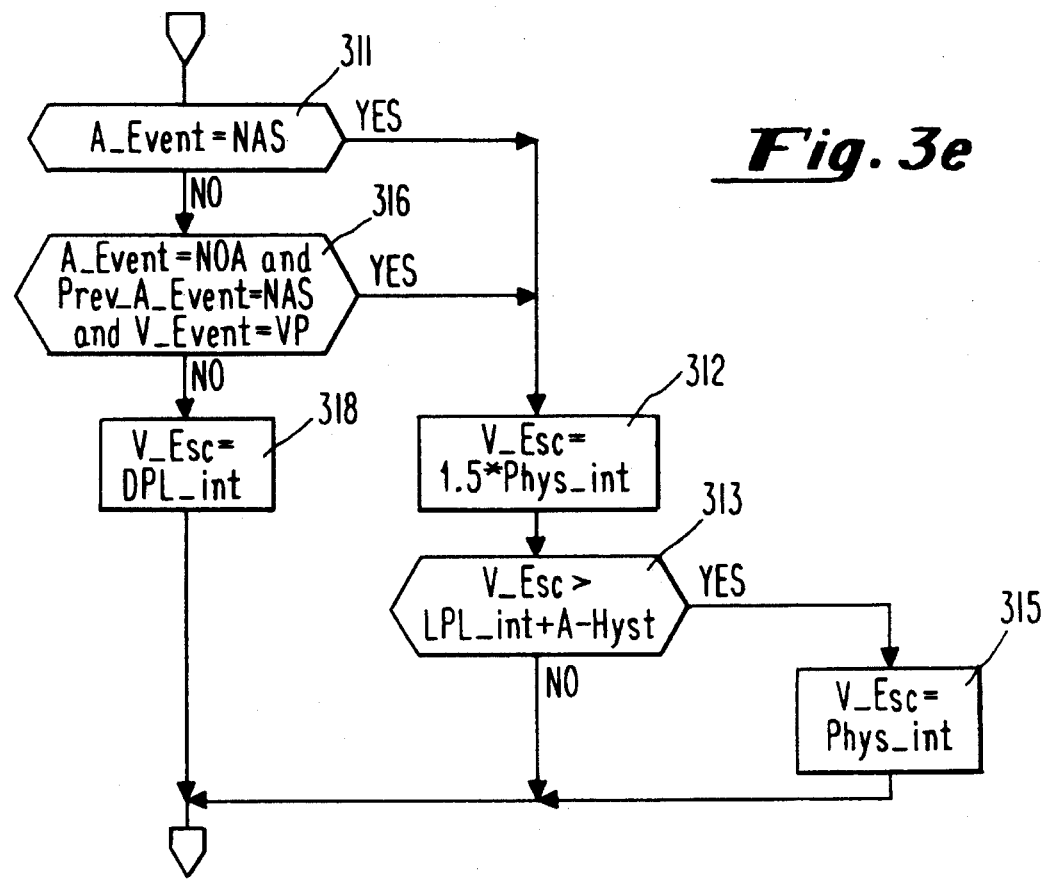
FIG. 3e is a simple flow diagram of a second undersense reaction algorithm for use with the pacemaker of this invention.
Figures 3F, 3G:
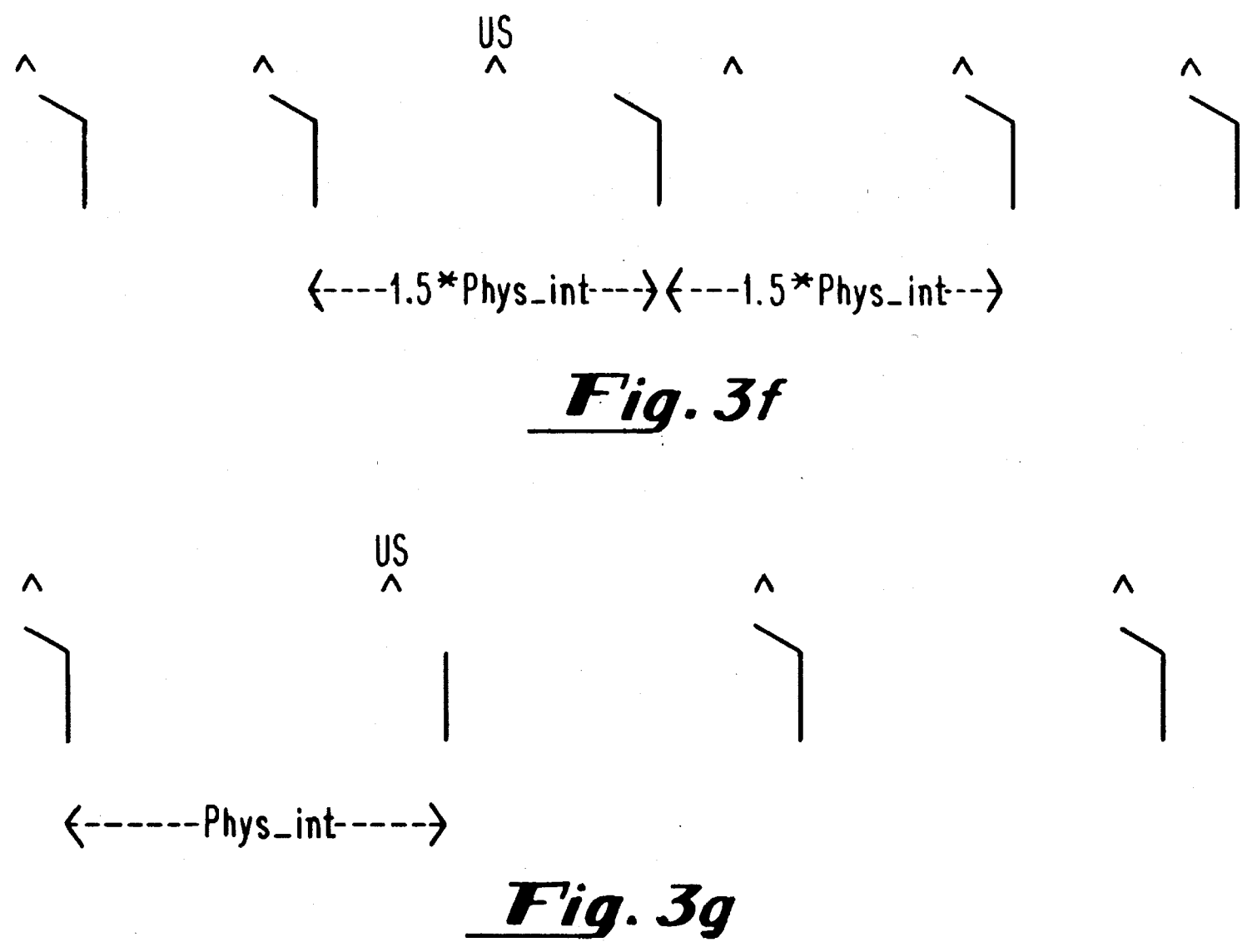

If the selection made at of block 71 of FIG. 2 directs the pacemaker to block 73, the pacemaker selects an appropriate undersense algorithm. FIG. 3d is a first example of a simple algorithm, with the premise that the absence of an AS is due to an undersense. Here, the ventricular escape interval is set equal to 1.5 * phys_int for two cycles and is set equal to DPL_int thereafter. At 311, it is determined whether an NAS has occurred. If yes, at block 312, V_esc equals 1.5 * phys_int. Then, at 313, it is determined whether V_esc is greater than LPL_int+A_Hyst. If the answer is yes, the routine branches to block 314 and clamps V_esc at LPL_int+A_Hyst. Returning to block 311 of FIG. 3d, if there is no NAS, at 316 it is determined whether there has been an absence of an atrial event and the previous atrial event was an NAS and the last V event was a VP. If yes, the routine again branches to block 312, but if no, it goes to block 318, and sets the ventricular escape interval equal to the interval corresponding to the dynamic pacing limit. The advantage of the method of FIG. 3d is that it generally achieves resynchronization after a first US and a next AS which cannot be tracked, and allows for relatively large A rate variations. However, a disadvantage is that it can result in V rate variations of 33% in the event of an undersense, and it may not work if the ventricular escape interval needs to be clamped according to block 314. Referring to FIG. 3f, there is shown a timing diagram where a US occurs. Note that the next A sense after the VS cannot be tracked, since it occurs too early. Tracking is regained after two V pulses delivered at V_esc=1.5 * phys_int. FIG. 3e shows substantially the same algorithm as FIG. 3d. The difference is that where the algorithm of FIG. 3d clamps V_esc in block 313, the algorithm of FIG. 3e shows the alternative response of setting the V_esc equal to phys_int (or the interval corresponding to running average). The use of phys_int as the escape interval after an US has the disadvantage that it is effective only if the atrial rate is substantially constant. The advantage of this undersense reaction is that the V rate is kept substantially constant. It also has the advantages of allowing for immediate resynchronization on the next AS and of maintaining a normal AV delay even following an US. Because of these advantages the algorithm of FIG. 3e prefers the use of phys_int as an escape interval that is well-related to the atrial rate in block 315 instead of limiting V_esc to LPL_int+A_Hyst, an interval that is not specifically related to the average atrial rate at that moment. In FIG. 3g, corresponding to FIG. 3e, V_esc is not clamped but set equal to phys_int, which gives a good result since the atrial rate had been relatively constant.

Figure 3H:
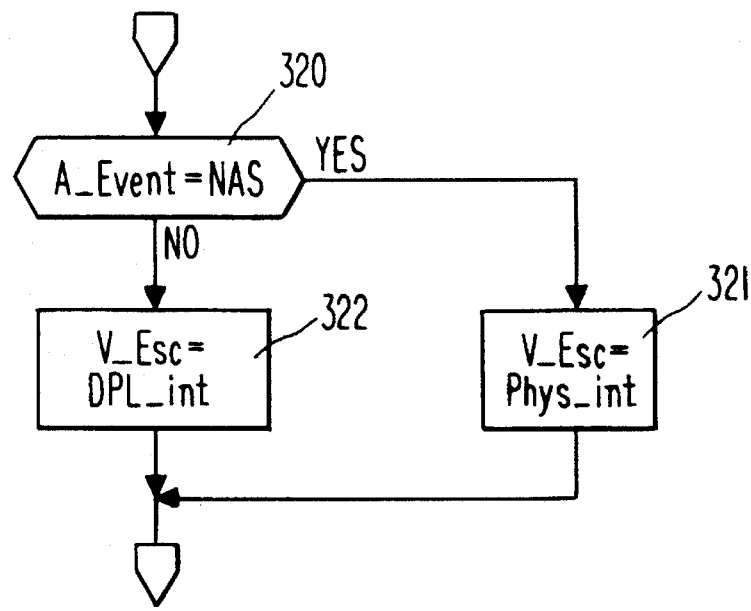
FIG. 3h is a simple flow diagram of a third undersense reaction algorithm for use with the pacemaker of this invention.
Figure 3I:
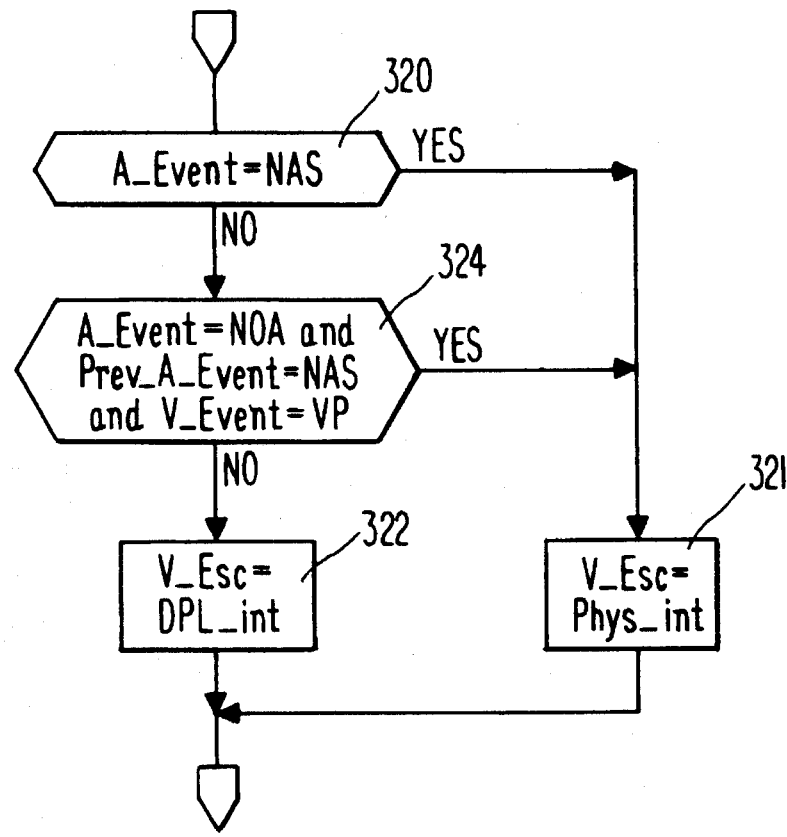
FIG. 3i is a simple flow diagram of a fourth undersense reaction algorithm for use with the pacemaker of this invention.

Referring to FIGS. 3h and 3i, there are shown two more examples of undersense algorithms where the ventricular escape interval is set equal to the phys interval for one or N cycles respectively. In FIG. 3h, at 320 it is determined whether there has been an NAS. If yes, the escape interval is set equal to the phys_int, as shown at 321. If no, the ventricular escape interval is set equal to the interval corresponding to DPL, as shown at 322. The algorithm of FIG. 3i modifies that of FIG. 3h by setting the ventricular escape interval equal to phys_int for N cycles, where N=2. Thus, if it is determined that there has not been an NAS at 320, the algorithm branches to 324, and determines whether the previous atrial event was an NAS and the following ventricular event was a VP. If yes, the algorithm branches to block 321, and again sets V_esc=phys_int. FIG. 3i can further be modified by making N greater than 2. Again the advantage of this undersense reaction is that the V rate is kept substantially constant and clamping is not necessary. Additionally, there is a normal AV delay and good resynchronization even in the case of an undersense. The disadvantage is that this algorithm is effective only if the atrial rate is substantially constant. FIG. 3j shows a timing diagram for the embodiments of FIGS. 3h and 3i, where there is a single undersense. FIGS. 3k and 3l show timing diagrams for the embodiments of FIG. 3h and FIG. 3i respectively, where there is a double undersense.

Figure 3M:
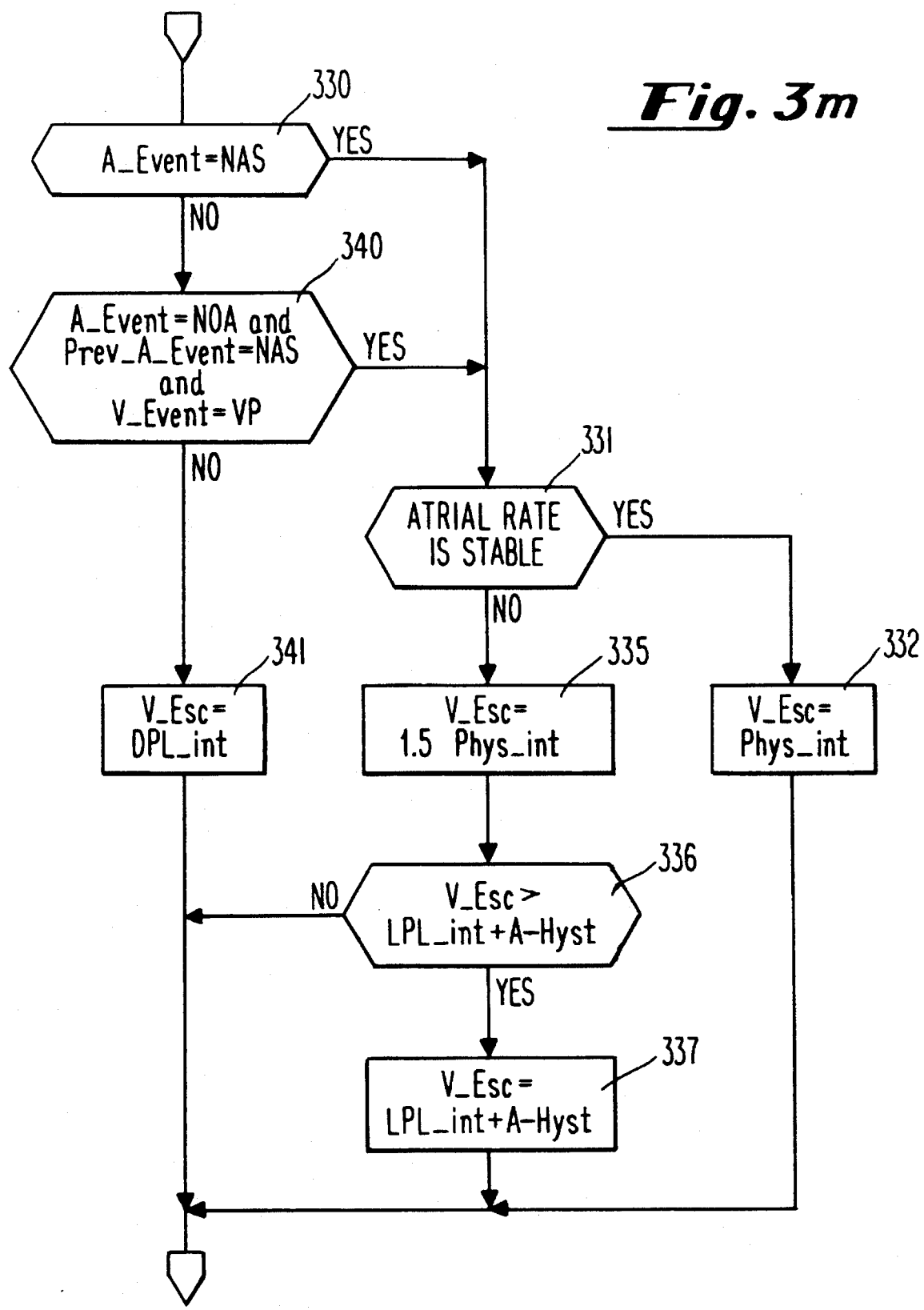
FIG. 3m is a simple flow diagram of a fifth undersense reaction algorithm for use with the pacemaker of this invention.

Another algorithm presenting an undersense reaction is illustrated in FIG. 3m, which provides for automatic switching between setting the ventricular escape interval at 1.5 * phys_int and phys_int. At 330, it is determined whether there has been an NAS. If yes, the routine branches to block 331 and determines whether the atrial rate is stable. Long-term stability can be determined utilizing scattergram data, such as disclosed in pending U.S. application Ser. No. 08/147,347, assigned to the same assignee, and incorporated herein by reference. Alternately, a register of the change in atrial rate for the last N cycles can be maintained, and a running average of such change made over those N cycles. If atrial rate is found to be stable, V_esc=phys_int at 332. If atrial rate is not stable, the algorithm goes to block 335, and sets V_esc=1.5 * phys_int. At 336, the V_esc is compared to LPL_int+A_Hyst, and if yes, V_esc is clamped at 337 to LPL_int+A_Hyst. As an alternative to the clamping at block 337, V_esc may be set equal to phys_int using block 332 again, analogous to the algorithm of FIG. 3e. Returning to 330, if there is no NAS, then at 340 it is determined whether the previous atrial event was an NAS and the previous ventricular event was a VP. If yes, the routine again branches to block 331, following which the ventricular escape interval is set either to 1.5 phys_int or simply phys_int. If the determination at block 340 is no, then the algorithm goes to 341 and sets V_esc equal to DPL_int. As seen, this third method automatically switches between the first method of FIGS. 3a–3c, or the second method of FIGS. 3d–3e, depending upon the stability or jitter of the atrial rate. The choice of one of these algorithms can be made automatically, based upon collected historic information, or it can be user selected. Thus, at block 73 of FIG. 2, there can be a further choice of a plurality of US reactions, or there can be a single user-selected algorithm which is inputted by the physician and stored for use by the pacemaker.

Having discussed illustrative algorithms for blocks 72, 73 and 74 of FIG. 2, we return to the discussion of FIG. 2. Following selection of an algorithm, at 76 the pacemaker waits for the next event, or absence of event. If a VS occurs, the pacemaker reacts in the normal manner to a VS, as indicated at 80. If an A sense occurs, the pacemaker reacts to such an A sense, as shown at 78, e.g., it tracks the A sense if it is physiological and not too early, and delivers a synchronous VP after an appropriate AV delay if no VS is detected earlier. If no signal is detected, the pacemaker proceeds at block 79 in accordance with the selected algorithm from block 72, 73 or 74. Thus, the event is determined as "none" in the absence of any signal sense prior to time out of V_esc. The pacemaker, at 76, may also be enabled to detect a US. This can be done by the subsystem of FIG. 4a, as discussed hereinafter. If an undersense is detected, the pacemaker goes to 77, where it is determined whether the US detection is reliable. The reliability test depends upon data derived from the subsystem of FIG. 4a, as well as data collected at block 83, as discussed below. If the US detection is reliable, the routine branches to block 78 and proceeds to react as though it is reacting to an A sense. Thus, the time of the undersense is taken as the time of an AS, for purposes of synchronous tracking. If the US detection is not reliable, the routine returns to block 76 and waits for a reliable event.

Following a reaction at 78, 79 or 80, the pacemaker proceeds to block 82 and updates historic information that it has obtained, and at block 83 updates the reliability of undersense detection. The logic involved in these two steps depends upon data obtained from the subsystem described in FIGS. 4a–4e, which is now examined.

Referring to FIG. 4a, there is shown a simplified circuit diagram for determining when a sensed atrial signal is a valid P-wave, and when there is an indication of an undersense. Two sense amplifiers 85, 86 receive the atrial signals, which are provided by the lead 64 which, as discussed above, may have a floating atrial electrode 55-A. The sense amplifiers have different sensitivities, $S_2$ having a greater sensitivity (lower threshold) than $S_1$. Thus, all signals having magnitudes above the threshold of $S_1$ will pass through both amplifiers 85 and 86, while signals having a magnitude below $S_1$ but above $S_2$ will pass only through amplifier 86. Amplifier 85 is a conventional A sense amplifier, with $S_1$ being set at a sensitivity to optimize detection of P-waves and rejection of noise. The outputs of the two amplifiers are inputted to timing logic circuit 87. Also, the current phys_int is inputted into logic block 87. If there is an input to 87 from both 85 (and logically also 86), it is concluded that the received signal is an A sense, or P-wave, and a logic output is provided as indicated. If, however, there is no input from amplifier 85, but there is an input from amplifier 86 which is found to define an A—A interval substantially equal to phys_int, then a US logic output it provided. The P and US logic signals, as well as the signals from amplifier 85, are inputted into a histogram generator 88, for generation of a P-wave histogram. There, the sensed P-waves are classified as to magnitude by conventional amplitude detection means, in a known manner. See, for example, U.S. Pat. No. 4,513,743, assigned to the same assignee, disclosing generation of histograms in a pacemaker.

Referring now to FIGS. 4b and 4c, there are shown two examples of P-wave amplitude histograms taken by the subsystem of FIG. 4a. On each, the sensitivities $S_1$ and $S_2$ are shown, one histogram bin containing counts of amplitudes between $S_2$ and $S_1$, which represents a count of US events. Note that $S_1$ cannot be made too sensitive, because this can lead to oversensing. On the other hand, $S_2$ can be made more sensitive because signals falling between $S_2$ and $S_1$ can be checked by verifying the coincidence of $S_2$ and $S_1$ signals, and by checking to see if $S_2$ signals (through amplifier 86) do not trigger much more often than $S_1$ signals (through amplifier 85). The histogram information, as illustrated in FIGS. 4b and 4c, is accumulated at block 82. Sensed P-waves are classified as to magnitude by conventional amplitude detection means. It is not necessary that every P-wave be so classified, as long as it is done on some regular sample basis. In the illustration of FIG. 4b, most of the P-waves have amplitudes in the bin just above sensitivity level $S_1$, and there are some undersenses shown in the shaded bin. This histogram profile indicates a distinct likelihood of undersensing. By contrast, the lower illustrated histogram of FIG. 4c indicates that relatively few P-waves have amplitudes in the bin just above $S_1$, suggesting a relatively low likelihood of undersensing and a higher likelihood that the absence of an AS represents true brady. Here, the bin between $S_1$ and $S_2$ is substantially empty, as illustrated.

Figure 4D:
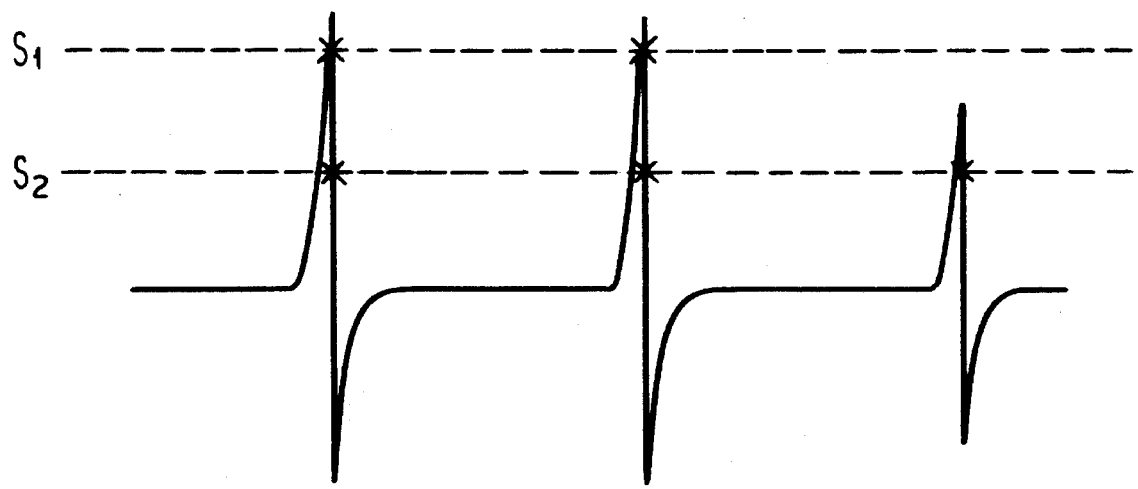
FIG. 4d is a timing diagram illustrating the operation of the sense amplifiers of FIG. 4a relative to P-wave amplitude.
Figure 4E:
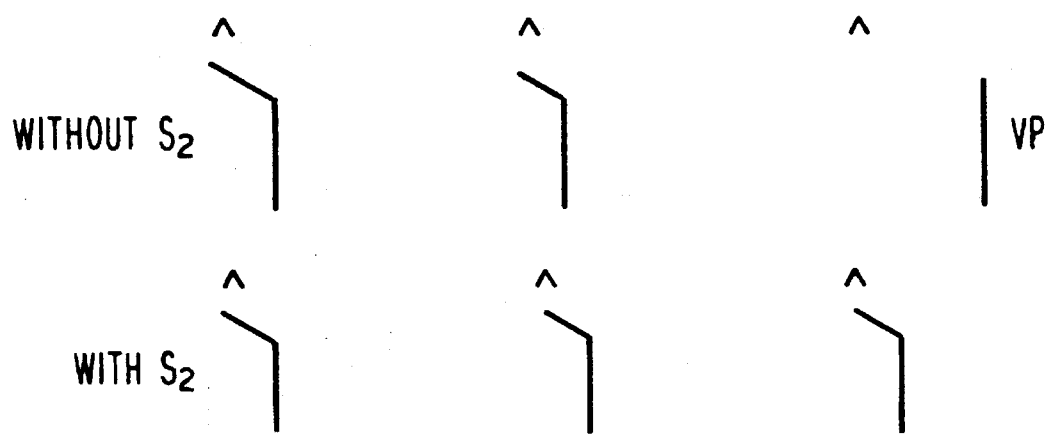
FIG. 4e is a pair of timing diagrams respectively illustrating operation with and without a second ($S_2$) signal amplifier.

Referring to FIGS. 4d and 4e, there are shown curves illustrating P-waves of different magnitudes relative to the $S_1$ and $S_2$ sensitivities. As illustrated in FIG. 4d, the first two P-waves have a peak amplitude greater than $S_1$, while the third P-wave has a magnitude above $S_2$ but below $S_1$. The first timing diagram of FIG. 4e represents operation with only amplifier 85 ($S_1$), and it is seen that after the first two P-waves are tracked, there is undersensing followed by a delivered stimulus at V_esc. However, when $S_2$ is also used, as in the lower timing diagram, the third P-wave is detected by $S_2$. Since it occurs at substantially the same interval as prior P-waves, it is treated as a detected undersense, and tracked as an A sense. See blocks 76, 77 and 78 of FIG. 2, and the above discussion. Thus, for the first two signals, there is a coincidence of signals inputted into timing logic block 87 of FIG. 4a, affirming the likelihood that the signal represents a true P-wave and not, for instance, noise sensed by the more sensitive circuit 86. With respect to the third signal, the pacemaker logic receives only the $S_2$ signal from circuit 86, and compares the timing of it with the current running average, or phys_rate. If, as illustrated, the $S_2$ signal occurs at about the phys_int, then it is deemed to be a P-wave, instead of noise or oversensing, and the pacemaker counts this as data indicating a US.

Referring now back to block 82 of FIG. 2, the criteria for updating the historic information can be reviewed. An undersense is likely to have occurred when AA_int is approximately 2 * phys_int AND/OR there are relatively many counts in the first bin above $S_1$ or in the bin between $S_2$ and $S_1$ in FIG. 4b; a brady occurrence is likely to have occurred when the atrial rate frequently drops below hysteresis limit, AND AA_int is not approximately 2 * phys_int OR AA_int has been approximately 2 * phys_int for a substantial number of successive beats (atrial rate really has dropped 50%). Also at block 82, for each cycle where a probable best reaction has been chosen at block 71, the pacemaker looks to see whether a brady or an undersense has been confirmed as likely to have occurred. A count is maintained of confirmed and unconfirmed selections.

At block 83, US detection is determined to be reliable when the following conditions are found:

There are many senses between $S_2$ and $S_1$, AND $S_2$ and $S_1$ trigger coincidentally most of the time, AND $S_2$ does not sense much more often than $S_1$, AND if $S_2$ senses and $S_1$ does not, the AA_int as measured by $S_2$ is approximately phys_int.

In the practice of the invention, the reliability data may be maintained by incrementing a first counter when the above criteria are fulfilled, and by incrementing a second counter when they are not fulfilled. If the first counter is found to be significantly higher than the second one, US detection is judged reliable. It is to be understood that this only an illustrative technique for maintaining reliability information.

Figures 5A, 5B:
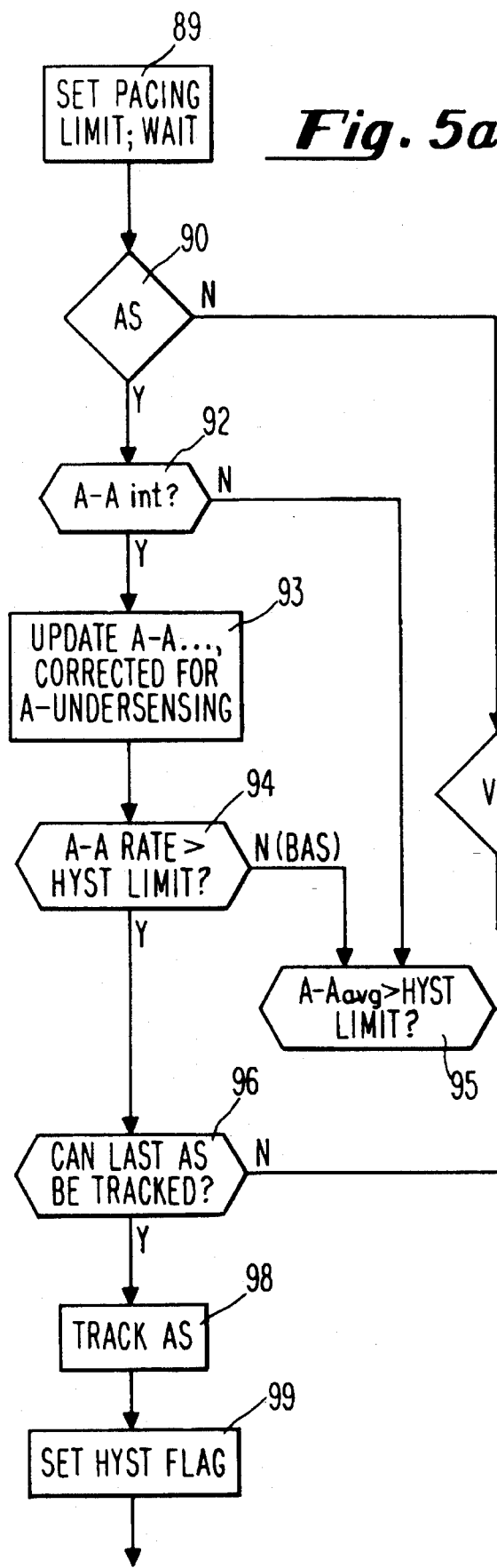

Referring now to FIGS. 5a and 5b, there is illustrated the logic of another algorithm which can be utilized for effectively extending, i.e., quickly returning to the hysteresis mode under circumstances where the pacemaker finds a likelihood of a US. This analysis depends upon predetermined criteria for calculating a running A-$A_{avg}$, corrected for atrial undersensing. In determining a running atrial rate, or $AA_{avg}$, the pacemaker looks for circumstances where an AS was missed, e.g., due to blanking or undersensing. If the current A—A interval is found to be approximately two times the running average interval, this suggests a single missed AS, perhaps due to blanking or undersensing. Under these circumstances, $AA_{avg}$ is not changed, i.e., the long interval is not used to update the average. Alternatively, when there is reason to assume that the long interval devided by 2 reflects the actual A—A interval, this corrected value is used to update $AA_{avg}$. This determination is thus similar to the updating of historic information discussed in connection with FIG. 2.

Referring now to FIG. 5a, the primary logical steps of a software embodiment for this embodiment of the pacemaker system of this invention are shown. At 89, the pacing limit is set, and the pacemaker then waits for the next event. The pacing limit is modified to be a hysteresis rate, Hyst limit, if the hysteresis flag is set. At 90, it is determined whether there has been an atrial sense. If no, the routine branches to 91, and determines whether there has been a ventricular sense. If yes, the cycle is complete and the routine exits; if no, the routine goes to block 97 and delivers a V pace at the pacing limit. Following delivery of a VP, the hysteresis flag is reset at block 100.

Going back to block 90, if there has been an atrial sense, at block 92 it is determined whether an A—A interval is available. The criteria for determining whether an A—A interval is "available" are set forth in FIG. 5b. Such an interval is deemed to be available either when there has been an atrial sense (AS) in the previous cycle, or, if there was no AS in the previous cycle but the previous cycle was commenced by tracking an AS. If there was no AS in the previous cycle, and the previous cycle was not initiated by tracking, then even though there has been an AS, an A—A interval is logically determined to be not available. If there is no A—A interval, the routine branches to 95; if yes, it goes to block 93. At block 93 the A—$A_{avg}$ is computed, corrected for A undersensing or blanking, subject to the above criteria. Following this, the routine goes to 94 and determines whether the A—A rate is greater than the hysteresis limit (DPL-A Hyst). If yes, the routine goes to 96 to determine whether the last atrial sense can be tracked. This determination includes the consideration of whether a V pace pulse at an interval AV after the A sense would yield a ventricular rate that was within prescribed limits. If the answer is yes, the routine goes to block 98 for tracking of the AS, following which the hyst flag is set at 99. If no, the routine branches to block 97 for delivery of a V pace at the pacing limit.

Going back to block 94, if the atrial rate is not greater than the hysteresis limit, suggesting a BAS, the routine branches to 95. At 95, it is determined whether the A—$A_{avg}$ is greater than the hysteresis limit. If no, indicating a real brady situation, the routine branches to 97 for delivery of a V pace at the pacing limit (either DPL or Hyst limit). If yes, this suggests that there has been an undersense, and the routine goes to 96 to determine whether the last AS can be tracked. Following this either the AS is tracked at block 98, or a V pace is delivered as indicated at block 97.

As is seen in connection with the following discussion of FIGS. 6a–6c and 7a, b, this algorithm contains the essential components of the algorithm of FIG. 2, i.e., information is obtained to indicate the likelihood of an undersense, and the pacemaker reacts to this likelihood. Thus, the determination of a running A—$A_{avg}$, which is corrected for US events, is a compiling of historic data. At block 95, the algorithm effectively determines whether brady or US is more likely, and reacts accordingly. Note that in this embodiment the reaction involves using atrial hysteresis, i.e., the pacemaker returns to hysteresis following a VP, to search for an underlying rate within the hysteresis band. Thus, the pacemaker initiates a "search" for signals below the pacing limit and within the hysteresis band, the initiation of the search being triggered by the determination of a likely US.

Figure 6A:
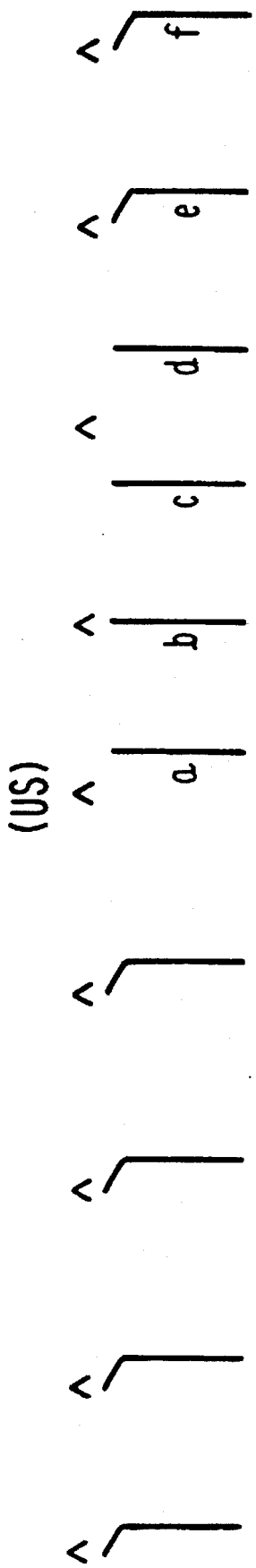
FIG. 6a is a first timing diagram of a series of cycles with an undersense event.
Figure 6B:
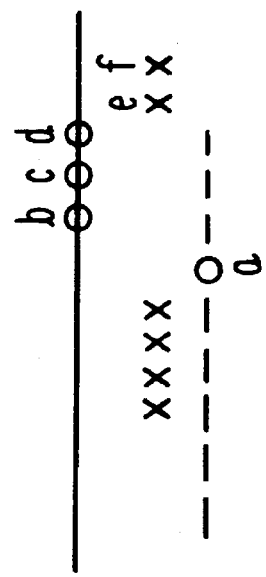
Figure 6C:
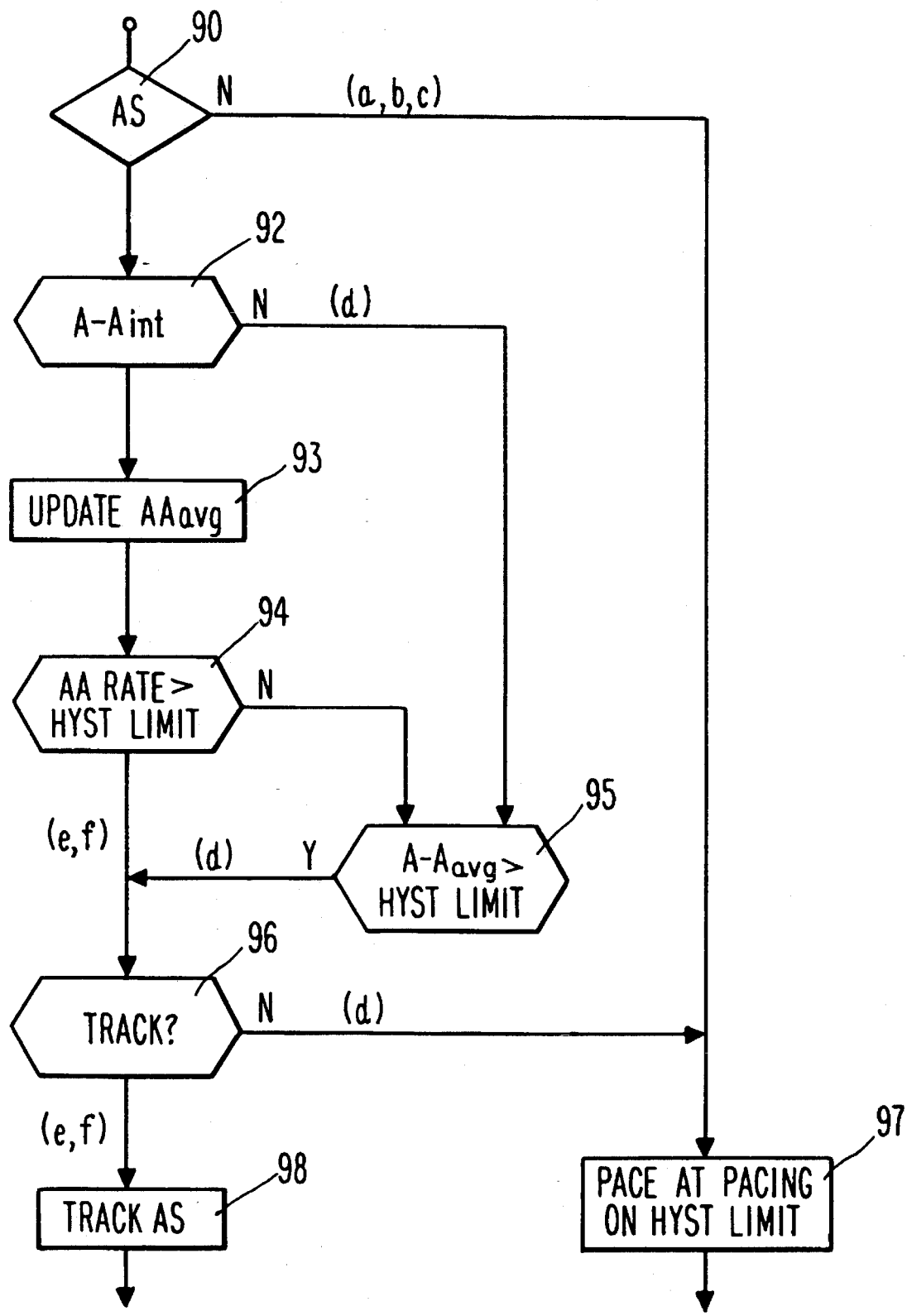

Referring now to FIGS. 6a, 6b, and 6c, there are illustrated diagrams showing the operation of the algorithm of FIG. 5a following undersensing of an atrial signal, specifically for a situation where the atrial rate is in the hysteresis band. Normally in that situation a US event removes hysteresis, and tracking is lost as long as the atrial rate remains in the hysteresis band. The timing diagram of FIG. 6a and the rate diagram of FIG. 6b, illustrate the sequence. As illustrated, there are initially four atrial senses within the hysteresis band ("x" in FIG. 6b), which are tracked by the pacemaker. Following this, there is an undersense (US) as indicated at "a", following which a ventricular pace pulse is delivered corresponding to the hysteresis limit. After this, the next three cycles terminate in ventricular pace pulses delivered at the pacing limit, as illustrated at b, c and d. Note that the atrial signal corresponding to b is not sensed because of blanking; and the sensed atrial signal between pulses c and d does not permit determination of an A—A interval. During this time, the atrial rate has in fact been substantially constant, and at "e" an atrial signal is sensed which defines an interval within the hysteresis limit. Consequently, events "e" and "f" result in tracked signals, and the pacemaker continues to track as long as the rate is maintained above the hysteresis limit. The logic corresponding each of these events is indicated in FIG. 6c, which repeats the pertinent decision blocks from FIG. 5a, and indicates the logic path for each respective event.

Figure 7A:
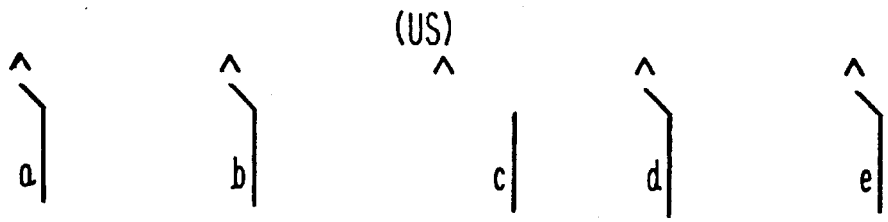
FIG. 7a is a second timing diagram of a series of cycles with an undersense event.
Figure 7B:
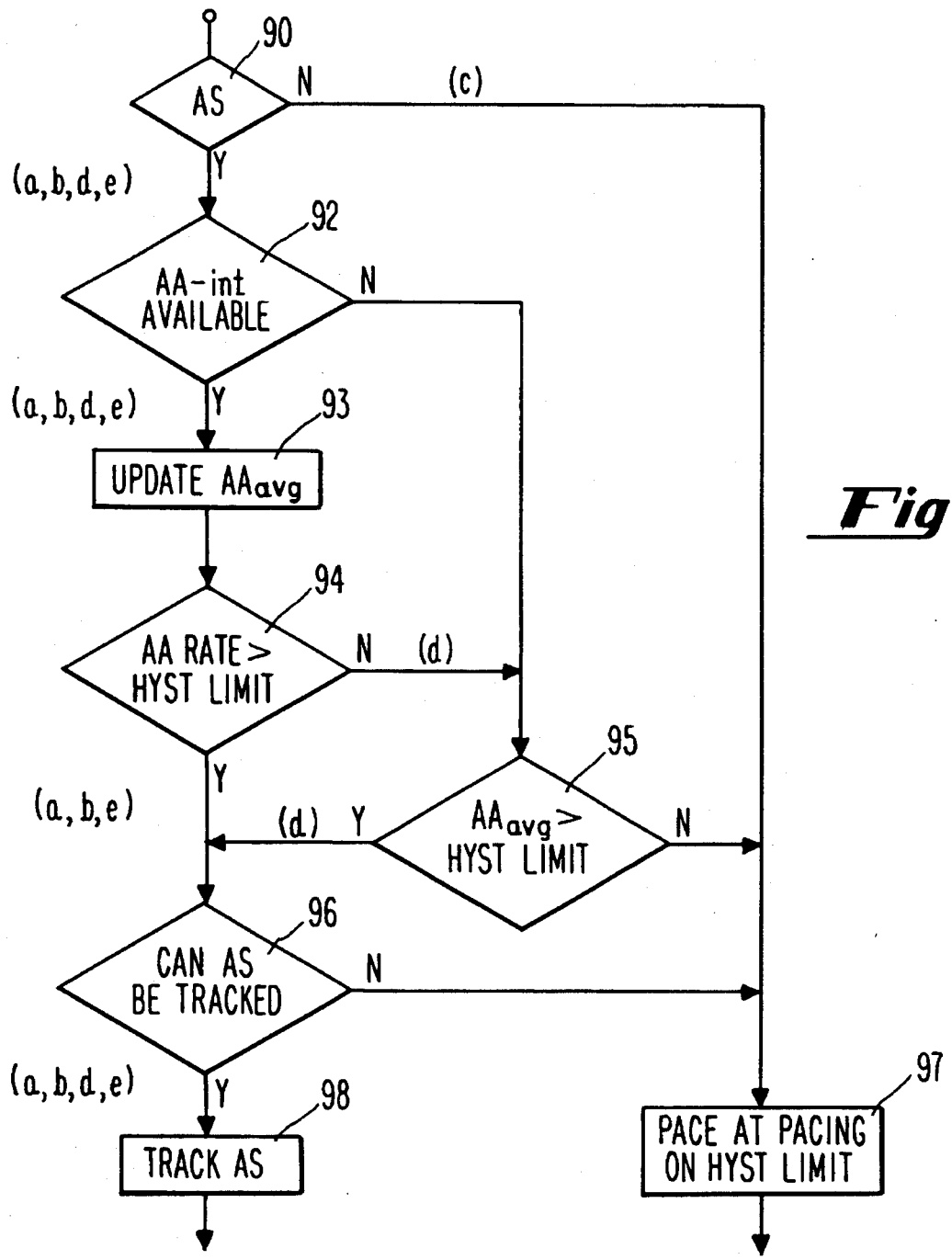

Referring now to FIGS. 7a and 7b, there is illustrated the reaction of the algorithm shown in FIG. 5a to a single US, where tracking is regained after just one VP at V__esc. Here, the first two atrial signals (a, b) are within the hysteresis band, and are tracked. Following an undersense, a VP (c) is delivered at V__esc. When the next P-wave is sensed, it is found to be at about 2 * A—$A_{avg}$. Thus, at 93 A—$A_{avg}$ is not changed. Even though A—A rate (of the last interval) is found to be less than the Hyst limit (at 94), the A—$A_{avg}$ is found to be greater than Hyst limit, at 95. At 96 it is determined that the AS can be tracked (not too early compared to the prior VP), and the synchronous VP is delivered at (d).

There has thus been illustrated a unique VDD(R) pacemaker system which is adapted to react optimally to undersense or brady situations. By accumulating historical information, the pacemaker can react in a preferred manner to fix the problem, i.e., it can react specifically to cure an undersense situation, or react in the normal manner for a brady situation. Although several specific examples of collecting historical data have been provided, it is to be understood that other equivalent techniques can be employed for collecting this information. Also, while several specific algorithms have been presented for reacting to probable undersense events, similar equivalent algorithms are within the scope of the invention.

What is claimed is:

1. A dual chamber cyclically operating pacemaker, having generator means for generating pace pulses for delivery to a patient's heart, atrial sense means for sensing atrial signals from said patient's atrium, said atrial sense means having some incidence of undersensing atrial signals, ventricular sense means for sensing ventricular signals from said patient's ventricle, and pace control means for controlling generation of pace pulses by said generator means in the absence of sensed heart signals, said pace control means characterized by:

brady reaction means for controlling the pacemaker to react with a predetermined brady response following a pacemaker cycle without a sensed atrial or ventricular signal;

undersense reaction means for controlling the pacemaker to react with a predetermined undersense response following a pacemaker cycle without a sensed atrial or ventricular signal; and selecting means for selecting one of said brady reaction means and said undersense reaction means for controlling the pacemaker following a pacemaker cycle without a sensed atrial or ventricular signal.

2. The pacemaker as described in claim 1, wherein said selecting means is operative each cycle of said pacemaker.

3. The pacemaker as described in claim 1, wherein said selecting means further comprises historical means for accumulating historical information relating to brady and undersense occurrences.

4. The pacemaker as described in claim 3, comprising first reliability means for determining the reliability of said historical information, as a predictor of the likelihood of brady and undersense occurrences.

5. The pacemaker as described in claim 4, comprising enabling means for enabling said selection means only when said historical information is determined to be reliable.

6. The pacemaker as described in claim 5, wherein said selecting means comprises means for analyzing said historical information to determine whether a brady response or undersense response is a preferred reaction following a heart cycle without a sensed atrial or ventricular signal.

7. The pacemaker as described in claim 1, further comprising undersense detecting means for detecting when an undersense has occurred, and wherein said undersense reaction means controls said pacemaker to respond to a said detected undersense as though it were an atrial sense.

8. The pacemaker as described in claim 7, comprising reliability means for determining the reliability of said undersense detecting.

9. The pacemaker as described in claim 1, wherein said pacemaker operates in the VDD mode, and said atrial sense means comprises a floating atrial electrode.

10. The pacemaker as described in claim 1, wherein said undersense reaction means comprises a software embodied algorithm defining said predetermined undersense response.

11. A dual chamber cyclically operating VDD mode pacemaker system, having ventricular generator means for generating pace pulses for delivery to a patient's ventricle, atrial sense means for sensing atrial signals from said patient's atrium, said atrial sense means comprising an electrode designed to float in said patient's atrium to pick up said atrial signals, ventricular sense means for sensing ventricular signals from said patient's ventricle, and pace control means for controlling generation of pace pulses by said ventricular generator means in the absence of sensed ventricular heart signals, said pace control means comprising:

undersense detection means for detecting when there has been an atrial signal that is not sensed by said atrial sense means;

reliability means for determining when said undersense detection is reliable;

atrial sense response means for responding to an sensed atrial signal with a predetermined tracking response; and undersense response means for enabling said atrial sense response means to respond to a reliable undersense detection as though it had been a sensed atrial signal.

12. The pacemaker system as described in claim 11, wherein said atrial sense means comprises a first sense amplifier with a first signal sensitivity, rate means for determining a recent physiological rate of sensed atrial signals, and wherein said undersense detection means comprises a second sense amplifier which receives said atrial signals and has a signal sensitivity permitting sensing of lower level signals than said first sense amplifier, determining means for determining when said second sense amplifier senses a signal and said first sense amplifier does not, and timing comparison means for comparing an atrial signal sensed only by said second sense amplifier with said recent physiological rate.

13. The pacemaker system as described in claim 12, wherein said timing comparison means has second determining means for determining an undersense when an atrial signal sensed only by said second sense amplifier occurs at about a time corresponding to said recent physiological rate.

14. The pacemaker system as described in claim 11, further comprising undersense reaction means for controlling the system to react with a predetermined undersense response following a heart cycle without an undersense detection or a sensed atrial or ventricular signal.

15. A dual chamber cyclically operating VDD mode pacemaker, having ventricular generator means for generating pace pulses for delivery to a patient's ventricle, atrial sense means for sensing atrial signals from said patient's atrium, ventricular sense means for sensing ventricular signals from said patient's ventricle, and pace control means for controlling generation of pace pulses by said ventricular generator means in the absence of sensed ventricular heart signals, said pace control means comprising:

first determining means for determining information relating to occurrences of bradycardia;

second determining means for determining information relating to occurrences of undersenses by said atrial sense means; and said pace control means comprising selecting means for selecting one of a plurality of respective predetermined responses to a condition where there is a pacemaker cycle without a sensed atrial or ventricular signal, such selecting being based upon said brady occurrence information and said undersense information.

16. A dual chamber cyclically operating VDD mode pacemaker, having ventricular generator means for generating pace pulses for delivery to a patient's ventricle, atrial sense means for sensing atrial signals from said patient's atrium, ventricular sense means for sensing ventricular signals from said patient's ventricle, and pace control means for controlling generation of pace pulses by said ventricular generator means in the absence of sensed ventricular heart signals, said pace control means comprising:

determining means for determining the relative likelihood of occurrences of brady and undersensing;

reaction means for providing a plurality of respective logic controlled reactions following a pacemaker cycle without a sensed atrial or ventricular signal; and selection means for selecting one of said plurality of reactions based on said determined likelihood.

17. The pacemaker as describe in claim 16, wherein at least one of said reactions assumes a brady event, and one of said reactions assumes an undersense event.

18. The pacemaker as described in claim 16, wherein said determining means comprises comparison means for comparing the latest interval between sensed atrial signals with a measure of the average interval just before said latest interval.

19. The pacemaker as described in claim 16, comprising storage means for storing user-inputted data and wherein said determining means determines said likelihood at least in part based upon said inputted data.

20. The pacemaker as described in claim 16, wherein said determining means comprises information means for cyclically accumulating information concerning the likelihood of brady and undersense events.

21. A VDD pacemaker, having A sense means for sensing atrial signals (A-sense), V sense for sensing ventricular signals (V sense), V generator means for generating ventricular pace pulses (V pace), pacing control means for controlling said V generator means to generate pace pulses, said pacing control means having tracking means for controlling said V generator to deliver a V pulse at a timed A-V interval following an A sense in the absence of an earlier V sense, pacing limit means for determining a normal pacing rate limit for generating V paces, and hysteresis limit means for determining a hysteresis rate limit for generating V paces, further comprising atrial rate means for determining a running measure of atrial rate which takes into account undersense (US) occurrences, comparison means for comparing said atrial rate measure with said hysteresis rate limit, and enabling means for enabling said tracking means for tracking of an atrial sense when said comparison indicates that said atrial measure is greater than said hysteresis limit.

22. The pacemaker as described in claim 21, wherein said atrial rate means comprises means for determining when the interval between two successive A senses is approximately twice said running measure, thereby indicating an undersense.

23. An implantable cardiac pacemaker system, having sense means for sensing natural heartbeats and generator means for generating pace pulses in the absence of a sensed heartbeat occurring within a predetermined rate range, and rate control means for controlling the rate of generated pace pulses, said rate control means having pacing limit means for normally setting the rate of pace pulses at a pacing limit, further comprising means for storing data representative of the rates of said sensed heartbeats, means operative following the absence of a sensed heartbeat to determine, based on said data, the likelihood of an underlying natural signal that was not sensed, and hysteresis means enabled when a said likelihood is determined to adjust the escape interval for the next generated pace pulse to correspond to a hysteresis rate which is below said pacing limit.

24. The pacemaker as described in claim 23, wherein said pacemaker system comprises a VDD dual chamber pacemaker, having A sense means for sensing atrial beats, V sense means for sensing ventricular beats, and V generator means for generating ventricular pace pulses at a rate controlled by said rate control means.

25. A VDD pacemaker, having A sense means for sensing atrial signals, V sense means for sensing ventricular signals, V generator means for generating ventricular pace pulses, rate control means for normally controlling said V generator means to generate pace pulses at a pacing rate limit, and tracking means for controlling said V generator to deliver V pace pulses at a timed A-V interval following A sense events, further comprising:

measure means for determining the atrial rates of sensed atrial signals and developing therefrom a running measure of atrial rate, hysteresis search means for adjusting said pacing rate limit to a hysteresis limit when enabled, and enabling means for enabling said hysteresis search means as a function of said atrial measure.

26. The VDD pacemaker as described in claim 25, wherein said measure means comprises undersense determining means for determining when it is likely that there was an undersense just prior to the most recent A sense, and for adjusting said running measure of atrial rate as a function of said determination.

27. A cyclically operating VDD pacemaker, having A sense means for sensing atrial signals, V sense means for sensing ventricular signals, V generator means for generating ventricular pace pulses, and tracking means for controlling said V generator to deliver V pace pulses at a timed A-V interval following A sense events, further comprising:

data means operative each cycle for storing data relating to predetermined events in such cycle;

interval means for generating an interval of time corresponding to a running rate average of recent physiological atrial signals;

determining means operative when there is a cycle in which there is no atrial sense for determining from said stored data whether a predetermined set of conditions is found; and V generator control means for controlling the rate of V pace pulses, having
  i. first means for normally setting the V_esc at a predetermined pacing limit in the absence of an atrial sense; and
  ii. second means for setting V_esc at 1.5 times said interval for N consecutive cycles when said conditions are determined.

28. The pacemaker as described in claim 27 wherein N equals 1.

29. The pacemaker as described in claim 27, wherein said V generator control means comprises means for setting V_esc at said predetermined pacing limit after passage of said N cycles and following a next cycle without a normal atrial sense.

\* \* \* \* \*

UNITED STATES PATENT AND TRADEMARK OFFICE
CERTIFICATE OF CORRECTION

PATENT NO. : 5,454,836
DATED : October 3, 1995
INVENTOR(S) : Johannes S. van der Veen et al.

It is certified that error appears in the above-indentified patent and that said Letters Patent is hereby corrected as shown below:

At column 5, line 35, "ks" should be --As--.

Signed and Sealed this

Seventh Day of May, 1996

Attest:

BRUCE LEHMAN

*Attesting Officer*  *Commissioner of Patents and Trademarks*